US007660621B2

(12) United States Patent
Skakoon et al.

(10) Patent No.: US 7,660,621 B2
(45) Date of Patent: Feb. 9, 2010

(54) MEDICAL DEVICE INTRODUCER

(75) Inventors: James G. Skakoon, St. Paul, MN (US);
Thomas I. Miller, Palm Bay, FL (US);
Matthew S. Solar, Indialantic, FL (US);
Gerald W. Mills, Palm Bay, FL (US);
Charles L. Truwit, Wayzata, MN (US)

(73) Assignee: Medtronic, Inc., Minneapolis, MN (US)

( * ) Notice: Subject to any disclaimer, the term of this patent is extended or adjusted under 35 U.S.C. 154(b) by 1085 days.

(21) Appl. No.: 09/827,266

(22) Filed: Apr. 5, 2001

(65) Prior Publication Data
US 2002/0010479 A1 Jan. 24, 2002

Related U.S. Application Data

(60) Provisional application No. 60/195,663, filed on Apr. 7, 2000.

(51) Int. Cl.
*A61F 11/00* (2006.01)
(52) U.S. Cl. .................. 600/417; 606/130; 606/108; 600/424
(58) Field of Classification Search ......... 600/407–482; 606/129, 130, 53–59, 108; 29/423, 426.1, 29/426.4, 428, 464
See application file for complete search history.

(56) References Cited
U.S. PATENT DOCUMENTS

| 1,129,333 | A | 2/1915 | Clark |
| 2,686,890 | A | 8/1954 | Davis |
| 3,016,899 | A | 1/1962 | Stenvall |
| 3,017,887 | A | 1/1962 | Heyer |
| 3,055,370 | A | 9/1962 | McKinney et al. |
| 3,115,140 | A | 12/1963 | Volkman |
| 3,135,263 | A | 6/1964 | Connelley, Jr. |
| 3,223,087 | A | 12/1965 | Vladyka et al. |
| 3,262,452 | A | 7/1966 | Hardy et al. |
| 3,402,710 | A | 9/1968 | Paleschuck |
| 3,444,861 | A | 5/1969 | Schulte |
| 3,457,922 | A | 7/1969 | Ray |

(Continued)

FOREIGN PATENT DOCUMENTS

DE        3108766        9/1982

(Continued)

OTHER PUBLICATIONS

"Fathom Remote Introducer", Image-Guided Neurologics, Inc., CNS Hynes Convention Center, 2 p., (Oct. 30-Nov. 4, 1999).

(Continued)

*Primary Examiner*—Brian Casler
*Assistant Examiner*—Amanda Lauritzen
(74) *Attorney, Agent, or Firm*—Harness, Dickey & Pierce, PLC

(57) ABSTRACT

An introducer is described that is coupled to a patient, specifically a patient's skull. The introducer may include an advancer that is remote from the patient, the advancer communicating with the introducer by means of a cable system. The introducer may also include a local position sensor that indicates the position of the primary medical device being introduced. The introducer may also include a frameless reference system that locates the primary medical device relative to a table that the patient is fixed to.

35 Claims, 9 Drawing Sheets

U.S. PATENT DOCUMENTS

| | | |
|---|---|---|
| 3,460,537 A | 8/1969 | Zeis |
| 3,508,552 A | 4/1970 | Hainault |
| 3,760,811 A | 9/1973 | Andrew |
| 3,817,249 A | 6/1974 | Nicholson |
| 3,893,449 A * | 7/1975 | Lee et al. .................... 600/459 |
| 3,981,079 A | 9/1976 | Lenczycki |
| 4,013,080 A | 3/1977 | Froning |
| 4,040,427 A | 8/1977 | Winnie |
| 4,230,117 A | 10/1980 | Anichkov |
| 4,318,401 A | 3/1982 | Zimmerman |
| 4,341,220 A | 7/1982 | Perry |
| 4,345,606 A | 8/1982 | Littleford |
| 4,418,894 A | 12/1983 | Mailliet et al. |
| 4,463,758 A | 8/1984 | Patil et al. |
| 4,579,120 A | 4/1986 | MacGregor |
| 4,592,352 A * | 6/1986 | Patil .......................... 606/130 |
| 4,598,708 A | 7/1986 | Beranek |
| 4,608,977 A | 9/1986 | Brown |
| 4,617,925 A | 10/1986 | Laitinen |
| 4,629,451 A | 12/1986 | Winters et al. |
| 4,638,798 A | 1/1987 | Shelden et al. |
| 4,699,616 A | 10/1987 | Nowak et al. |
| 4,705,436 A | 11/1987 | Robertson et al. |
| 4,706,665 A | 11/1987 | Gouda |
| 4,805,615 A | 2/1989 | Carol |
| 4,809,694 A | 3/1989 | Ferrara |
| 4,826,487 A | 5/1989 | Winter |
| 4,883,053 A | 11/1989 | Simon |
| 4,955,891 A | 9/1990 | Carol |
| 4,998,938 A | 3/1991 | Ghajar et al. |
| 5,027,818 A | 7/1991 | Bova et al. |
| 5,030,223 A | 7/1991 | Anderson et al. |
| 5,065,761 A | 11/1991 | Pell |
| 5,078,140 A | 1/1992 | Kwoh |
| 5,080,662 A | 1/1992 | Paul |
| 5,116,345 A | 5/1992 | Jewell et al. |
| 5,154,723 A | 10/1992 | Kubota et al. ............... 606/130 |
| 5,163,430 A | 11/1992 | Carol |
| 5,201,742 A | 4/1993 | Hasson |
| 5,207,688 A | 5/1993 | Carol |
| 5,246,448 A | 9/1993 | Chang |
| 5,257,998 A | 11/1993 | Ota et al. |
| 5,263,956 A | 11/1993 | Nobles |
| 5,269,305 A | 12/1993 | Corol |
| 5,279,309 A | 1/1994 | Taylor et al. |
| 5,279,575 A | 1/1994 | Sugarbaker |
| 5,280,427 A | 1/1994 | Magnusson et al. |
| 5,300,080 A | 4/1994 | Clayman et al. |
| 5,306,272 A | 4/1994 | Cohen et al. |
| 5,330,485 A | 7/1994 | Clayman et al. |
| 5,366,446 A | 11/1994 | Tal et al. |
| 5,375,588 A | 12/1994 | Yoon |
| 5,380,302 A | 1/1995 | Orth |
| 5,383,454 A | 1/1995 | Bucholz |
| 5,394,457 A | 2/1995 | Leibinger et al. |
| 5,405,330 A | 4/1995 | Zunitch et al. |
| 5,452,720 A | 9/1995 | Smith et al. |
| 5,464,446 A | 11/1995 | Dressen et al. |
| 5,474,564 A | 12/1995 | Clayman et al. |
| 5,483,961 A | 1/1996 | Kelly et al. |
| 5,517,990 A | 5/1996 | Kalfas et al. |
| 5,541,377 A | 7/1996 | Stuhlmacher |
| 5,572,905 A | 11/1996 | Cook, Jr. |
| 5,572,999 A | 11/1996 | Funda et al. |
| 5,575,798 A | 11/1996 | Koutrouvelis |
| 5,618,288 A | 4/1997 | Calvo |
| 5,639,276 A | 6/1997 | Weinstock et al. |
| 5,643,286 A | 7/1997 | Warner et al. ............... 606/130 |
| 5,649,936 A | 7/1997 | Real |
| 5,658,272 A | 8/1997 | Hasson .......................... 606/1 |
| 5,667,514 A | 9/1997 | Heller ........................ 606/108 |
| 5,695,501 A | 12/1997 | Carol et al. |
| 5,713,858 A | 2/1998 | Heruth et al. |
| 5,755,697 A | 5/1998 | Jones et al. |
| 5,776,144 A | 7/1998 | Leysieffer et al. ........... 606/130 |
| 5,788,713 A | 8/1998 | Dubach et al. |
| 5,807,033 A | 9/1998 | Benway |
| 5,810,712 A | 9/1998 | Dunn |
| 5,817,106 A | 10/1998 | Real ............................ 606/130 |
| 5,823,975 A | 10/1998 | Stark et al. |
| 5,833,627 A | 11/1998 | Shmulewitz et al. ......... 600/562 |
| 5,843,150 A | 12/1998 | Dressen et al. |
| 5,865,817 A | 2/1999 | Moenning et al. |
| 5,865,842 A | 2/1999 | Knuth et al. |
| 5,871,487 A | 2/1999 | Warner et al. |
| 5,891,157 A | 4/1999 | Day et al. |
| 5,927,277 A | 7/1999 | Baudino et al. |
| 5,950,629 A * | 9/1999 | Taylor et al. ................. 128/897 |
| 5,954,687 A | 9/1999 | Baudino |
| 5,957,933 A | 9/1999 | Yanof et al. |
| 5,957,934 A * | 9/1999 | Rapoport .................... 606/130 |
| 5,964,705 A * | 10/1999 | Truwit et al. ................. 600/423 |
| 5,980,535 A | 11/1999 | Barnett et al. ............... 606/130 |
| 5,984,930 A * | 11/1999 | Maciunas et al. ............ 606/130 |
| 5,993,463 A * | 11/1999 | Truwit ........................ 606/130 |
| 6,018,094 A | 1/2000 | Fox |
| 6,024,729 A | 2/2000 | Dehdashtian et al. |
| 6,039,725 A | 3/2000 | Moenning et al. |
| 6,044,304 A | 3/2000 | Baudino |
| 6,071,288 A | 6/2000 | Carol et al. |
| 6,079,681 A | 6/2000 | Stern et al. |
| 6,110,182 A | 8/2000 | Mowlai-Ashtiani |
| 6,117,143 A | 9/2000 | Hynes et al. |
| 6,135,946 A * | 10/2000 | Konen et al. ................. 600/117 |
| 6,179,826 B1 | 1/2001 | Aebischer et al. |
| 6,195,577 B1 * | 2/2001 | Truwit et al. ................. 600/411 |
| 6,206,890 B1 * | 3/2001 | Truwit ........................ 606/130 |
| 6,210,417 B1 | 4/2001 | Baudino et al. |
| 6,231,526 B1 * | 5/2001 | Taylor et al. ................. 600/587 |
| 6,238,402 B1 * | 5/2001 | Sullivan et al. ............... 606/108 |
| 6,254,532 B1 | 7/2001 | Paolitto et al. |
| 6,257,407 B1 * | 7/2001 | Truwit et al. ................. 206/320 |
| 6,261,300 B1 | 7/2001 | Carol et al. |
| 6,267,769 B1 * | 7/2001 | Truwit ........................ 606/130 |
| 6,267,770 B1 * | 7/2001 | Truwit ........................ 606/130 |
| 6,273,896 B1 | 8/2001 | Franck et al. |
| 6,290,644 B1 | 9/2001 | Green et al. |
| 6,298,262 B1 | 10/2001 | Franck et al. ............... 600/426 |
| 6,321,104 B1 | 11/2001 | Gielen et al. |
| 6,327,491 B1 | 12/2001 | Franklin et al. |
| 6,356,792 B1 | 3/2002 | Errico et al. |
| 6,368,329 B1 * | 4/2002 | Truwit ........................ 606/130 |
| 6,400,992 B1 | 6/2002 | Borgersen et al. |
| 6,457,963 B1 | 10/2002 | Tawara et al. |
| 6,482,182 B1 | 11/2002 | Carroll et al. |
| 6,491,699 B1 | 12/2002 | Henderson et al. |
| 6,537,232 B1 * | 3/2003 | Kucharczyk et al. ......... 600/561 |
| 6,546,279 B1 * | 4/2003 | Bova et al. .................. 600/429 |
| 6,547,795 B2 | 4/2003 | Schneiderman |
| 6,556,857 B1 | 4/2003 | Estes et al. |
| 6,609,020 B2 | 8/2003 | Gill |
| 6,610,100 B2 | 8/2003 | Phelps et al. |
| 6,632,184 B1 * | 10/2003 | Truwit ........................ 600/585 |
| 6,655,014 B1 | 12/2003 | Babini |
| 6,662,035 B2 | 12/2003 | Sochor |
| 6,676,669 B2 | 1/2004 | Charles et al. |
| 6,706,050 B1 | 3/2004 | Giannadakis |
| 6,726,678 B1 * | 4/2004 | Nelson et al. ............. 604/891.1 |
| 6,746,471 B2 | 6/2004 | Mortier et al. |
| 6,752,812 B1 * | 6/2004 | Truwit ........................ 606/130 |
| 6,773,443 B2 * | 8/2004 | Truwit et al. ................. 606/169 |
| 6,782,288 B2 * | 8/2004 | Truwit et al. ................. 600/429 |
| 6,802,323 B1 * | 10/2004 | Truwit et al. ................. 134/117 |
| 6,913,478 B2 | 7/2005 | Lamirey et al. |

| | | | |
|---|---|---|---|
| 6,944,895 B2* | 9/2005 | Truwit | 5/601 |
| 6,960,216 B2 | 11/2005 | Kolb et al. | |
| 7,204,840 B2 | 4/2007 | Skakoon et al. | |
| 7,479,146 B2 | 1/2009 | Malinowski | |
| 2001/0014771 A1* | 8/2001 | Truwit et al. | 600/417 |
| 2001/0037524 A1* | 11/2001 | Truwit | 5/601 |
| 2002/0019641 A1* | 2/2002 | Truwit | 606/130 |
| 2002/0022847 A1 | 2/2002 | Ray et al. | |
| 2002/0052610 A1* | 5/2002 | Skakoon et al. | 606/129 |
| 2002/0077646 A1* | 6/2002 | Truwit et al. | 606/170 |
| 2002/0156372 A1* | 10/2002 | Skakoon et al. | 600/431 |
| 2003/0079287 A1* | 5/2003 | Truwit | 5/601 |
| 2003/0187351 A1 | 10/2003 | Franck et al. | |
| 2003/0208122 A1* | 11/2003 | Melkent et al. | 600/426 |
| 2004/0059260 A1* | 3/2004 | Truwit | 600/585 |
| 2004/0176750 A1* | 9/2004 | Nelson et al. | 604/891.1 |
| 2004/0243147 A1* | 12/2004 | Lipow | 606/130 |
| 2004/0255991 A1* | 12/2004 | Truwit et al. | 134/117 |
| 2004/0260323 A1* | 12/2004 | Truwit et al. | 606/170 |
| 2007/0250078 A1* | 10/2007 | Stuart | 606/130 |
| 2007/0299427 A1* | 12/2007 | Yeung et al. | 606/1 |
| 2008/0004632 A1* | 1/2008 | Sutherland et al. | 606/130 |

FOREIGN PATENT DOCUMENTS

| | | |
|---|---|---|
| DE | 29612100 | 9/1996 |
| DE | 19726141 | 1/1999 |
| DE | 19826078 | 8/1999 |
| DE | 19808220 | 9/1999 |
| DE | 19820808 | 11/1999 |
| EP | 0724865 | 8/1996 |
| EP | 0832611 A2 | 4/1998 |
| EP | 0904741 A2 | 3/1999 |
| GB | 2237993 A | 5/1991 |
| GB | 2329473 A | 3/1999 |
| GB | 2346573 | 8/2000 |
| WO | WO-8809151 | 12/1988 |
| WO | WO-95/22297 A1 | 8/1995 |
| WO | WO-96/10368 | 4/1996 |
| WO | 97/03609 | 2/1997 |
| WO | WO-97/21380 A2 | 6/1997 |
| WO | WO-98/17191 A1 | 4/1998 |
| WO | WO-98/25535 A1 | 6/1998 |
| WO | WO-9851229 | 11/1998 |
| WO | WO-00/01316 A1 | 1/2000 |
| WO | WO-01/49197 A1 | 7/2001 |
| WO | WO-0176498 | 7/2001 |

OTHER PUBLICATIONS

Grady, M., et al., "Nonlinear Magnetic Stereotaxis: Three-Dimensional, in vivo Remote Magnetic Manipulation of a Small Object in Canine Brain", *Medical Physics*,17 (3), (May/Jun. 1990), pp. 405-415.

Hata, N., et al., "Needle Insertion Manipulator for CT- and MR-Guided Stereotactic Neurosurgery", *Interventional MR: Techniques and Clinical Experience*, St. Louis : London : Mosby ; Martin Dunitz, F. Jolesz and I. Young, eds., (1998), 99-106.

Hirschberg, H., et al., "Image-guided neurosurgery—MR compatible stereotactic equipment", http:www.medinnova.no/English/P51466ster.html, (Mar. 29, 2001), 1 p.

Leggett, W. B., et al., "Surgical Technology—The Viewing Wand: A New System for Three-Dimensional Computed Tomography-Correlated Intraoperative Localization", *Current Surgery*, (Dec. 1991), 674-678.

Oliver, L., "Cup-And-Ball Chemopallidectomy Apparatus", (1958), p. 401.

Sandeman, D. S., et al., "Advances in image-directed neurosurgery: Preliminary experience with the ISG Viewing Wand compared with the Leksell G frame", *British Journal of Neurosurgery*, 8, (199), pp. 529-544.

Yeh, H.-S., et al., "Implantation of intracerebral depth electrodes for monitoring seizures using the Pelorus stereotactic system guided by magnetic resonance imaging", *J. Neurosurg.*, 78, (1993), pp. 138-141.

Zinreich, S. J., et al., "Frameless Sterotaxic Integration of CT Imaging Data: Accuracy and Initial Applications", *Radiology*, 188 (3), (1993), pp. 735-742.

"Possible Existence of Common Internalization Mechanisms among Arginine-rich Peptides", Suzuki, T. et al., Journal of Biological Chemistry, vol. 277, No. 4 (2002) pp. 2437-2443.

Dyer, P.V., et al., "The ISG Viewing Wand: an Application to Atlanto-Axial Cervical Surgery Using the Le for I Maxillary Osteotomy", British Journal of Oral and Maxillofacial Surgery, 33, (1995), 370-374.

Gehring, W. J., "Homeodomain Proteins", Annu. Rev. Biochem., vol. 63 (1997) pp. 487-526.

Grady, M., et al., "Magnetic Stereotaxis System for Neurosurgical Procedures", Proc. 37th International Instrumentation Symp., Sand Diego, CA (May 1991), 665-675.

Mannervik, M., "Target genes of homeodomain proteins", BioEssays vol. 21.4 (Apr. 1999) pp. 267-270.

Patikoglou, G. et al., "Eukaryotic Transcription Factor-DNA Complexes", Annual Review of Biophysics and Biomolecular Structure vol. 26 (1997) pp. 289-325.

Stein, S. et al., "Checklist: Vertebrate homeobox genes", Mechanisms of Development, vol. 55, No. 1 (Mar. 1996) pp. 91-108.

Vollmer, J. et al., "Homeobox Genes in the Developing Mouse Brain", Journal of Neurochemistry, vol. 71, No. 1 (Jul. 1998) pp. 1-19.

Wolberger, C., "Homeodomain Interactions", Current Opinion in Structural Biology vol. 6, No. 1 (Feb. 1996) pp. 62-68.

"Inomed Competence in Neurophysiologic Monitoring", http://www.inomed.com/english/index.htm, (observed Mar. 23, 2004), 2 pgs.

"MicroTargeting® Precision Guidance Using Microelectrode Recording", (Aug. 15, 2003), 5 pgs.

Franck, Joel, et al., "microTargeting® Platform incorporating StarFix™ guidance", *microTargeting*, 3 pgs.

Hirschberg, H., et al., "Image-Guided Neurosurgery—MR compatible stereotactic equipment", http:www.medinnova.no/English/P51466ster.html. (Mar. 29, 2001), 1p.

International Search Report and Written Opinion for PCT/US05/43651 mailed May 8, 2008.

Ritter, R., et al., "Stereotaxie Magnetique: Deplacement D'Implants dans le Cerveau, Assistes par Ordinateur et Guides par Imagerie", Innovation et Technologie en Biologie et Medecine, 13, (1992), 437-449.

* cited by examiner

MEDICAL DEVICE INTRODUCER

CROSS REFERENCE TO RELATED APPLICATION

This application claims priority to Provisional Application No. 60/195,663, filed Apr. 7, 2000.

BACKGROUND OF THE INVENTION

1. Field of the Invention

The present invention relates to medical devices. Specifically, the invention relates to inserting medical devices into a patient where the medical devices may be used in conjunction with magnetic resonance imaging.

2. Background of the Invention

An introducer is a secondary medical device that may be used in a surgical procedure to move a primary medical device into the patient. The introducer may be attached to a third device called a trajectory guide that positions the introducer in the direction of the area to be explored in the patient. The primary medical device may include, but is not limited to: a catheter with drug delivery capability; a tissue removal instrument such as a laser; an instrument for attaching an electrode; etc.

The alignment of an introducer may be controlled relative to the patient by the trajectory guide. Movement of the primary medical device relative to the patient is restricted once the introducer has been aligned. A translation range of motion of the introducer in operation is generally fixed in two coordinate axes, and limited to linear motion along one axis, into the patient. The introducer controls the linear motion along this single axis.

An introducer is used primarily in procedures where precise location of the primary medical device is critical, for example, brain surgery. Different variations of introducers are currently being used for procedures such as neurosurgery.

Typically, the patient is prepared by first fixing the patient in a location on an operating table surface. Conventionally, the skull of the patient is fixed to the table in order to keep the brain located relative to the operating table surface. A trajectory guide is then conventionally mounted on a fixture on the operating table. The patient may then be operated on directly, or the patient may be positioned in a magnetic resonance imaging (MRI) station such as a long bore MR scanner. An MR tube is used in cases where a focused area of the brain is to be imaged during the surgery. Next an opening in the skull is made, and the trajectory guide is aligned with the area of the brain to be explored.

Using one prior variation, the introducer is then attached to the trajectory guide, and the desired primary medical device is attached to the introducer. The first variation introducer includes a stepper motor, controlled by a computer, that drives the primary medical device into the patient. However, the stepper motor variation is relatively heavy and expensive. The weight of the unit requires a substantial support frame attached to the operating table to ensure that this introducer does not move during the procedure. Additionally, time consumed in re-sterilization between procedures means that this variation is frequently not available for use. The stepper motor variation is also not compatible with an MR tube environment.

A method that can be used in conjunction with an MR tube environment is "free-hand" introduction. Unfortunately, with this method, the surgeon cannot view the patient and the primary medical device in "real time." This is because the surgeon cannot simultaneously both view the MR display screen and operate the introducer. In real time imaging, the patient is inside an MR scanner, such as a long bore MR scanner. In order to view the MR image of the patient, the surgeon must be outside the long bore MR scanner, looking at the display screen. At the same time, in order to introduce the primary medical device, the surgeon must be near the patient, and not in a position to adequately view the display screen.

A variation of introducer that has been used to overcome the real time imaging insertion problem uses hydraulic lines to remotely control the introducer. The setup of the patient in this variation is the same, but the introducer further includes a remote actuation unit and hydraulic lines that lead from the remote actuation unit to the introducer. With the hydraulic variation, the surgeon can view the patient within the long bore MR tube, and at the same time the surgeon can actuate the introducer to move the primary medical device into the patient.

A significant problem with the hydraulic introducer is that this device is expensive and contains many complicated components that must be inspected and maintained. Another problem with the hydraulic variation is that the hydraulic fluid used to actuate this variation of remote introducer must be sealed and sterile or it must be re-sterilized after each surgical procedure.

What is needed is an inexpensive, lightweight introducer that can be used once and disposed of. What is also needed is an inexpensive introducer device that requires a minimal number of components to maintain, and requires minimal patient set up equipment to further minimize costs. What is also needed is an inexpensive remote introducer that allows the surgeon to both view the patient in real time, and actuate the remote introducer to move the primary medical device into the patient.

SUMMARY OF THE INVENTION

The invention includes an introducer that is inexpensive to manufacture with a minimum number of components. The introducer includes a guide unit and a holder assembly that moves along the guide unit. The holder assembly is capable of receiving a primary medical device and introducing the primary medical device into a patient. The invention includes an advancer that may be remote from the introducer. In the case of a remote advancer, the advancer may be coupled to the introducer by a cable system.

The invention may include a position scale that is located on the advancer, or it may include a position sensor that is mounted locally on the introducer. The position sensor may include a potentiometer or an encoder or similar device. The invention may also include a centering plate that aids in alignment of the primary medical device being used.

The advancer may include a thumb wheel that advances the primary medical device into the patient by rotating the thumb wheel. The advancer may further include a locking mechanism that fixes the thumb wheel in place when not in use. The locking mechanism may operate in either a "free wheeling" mode or a "discrete step" mode. The advancer may also include an indicator scale that shows the depth of the primary medical device in the patient.

The invention may include an introduction system that includes an introducer, a trajectory guide, and a primary medical device. The introduction system may also include a frameless reference system.

DESCRIPTION OF THE INVENTION

An introducer is described below that is lightweight, inexpensive to manufacture, and is comprised of a minimum number of moving parts. As a result it may be used disposably and will not require re-sterilization. One embodiment is also a remote introducer that may be actuated from a remote location while a patient is inside a device such as a long bore MR tube. Other embodiments include elements that reference the relative position of a primary medical device being inserted into a patient. Still another embodiment includes an introducer that is mounted directly to a patient instead of mounting to a fixture on a table surface.

Figure 1:
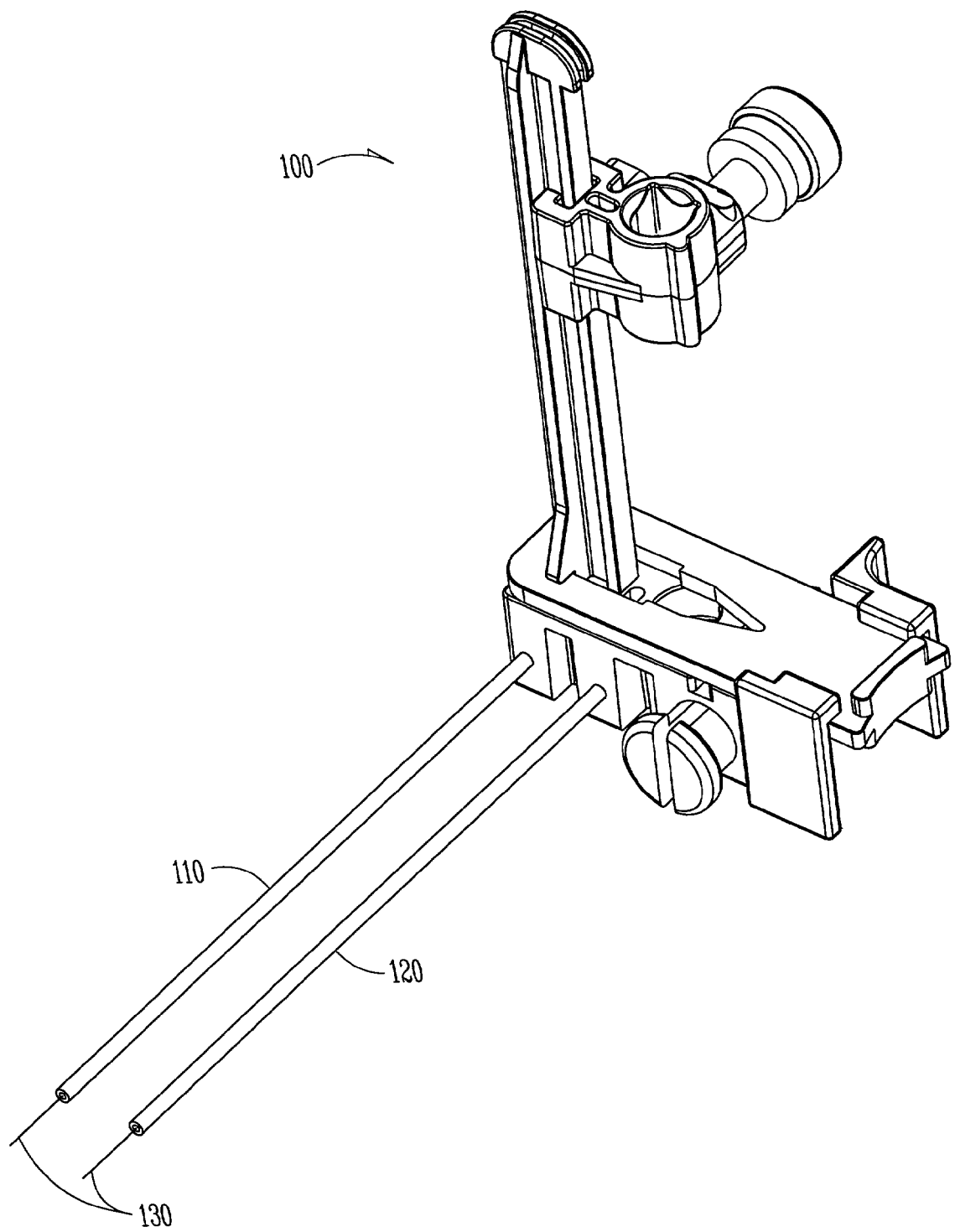
FIG. 1 shows a perspective view of an introducer device according to the invention.
Figure 2:
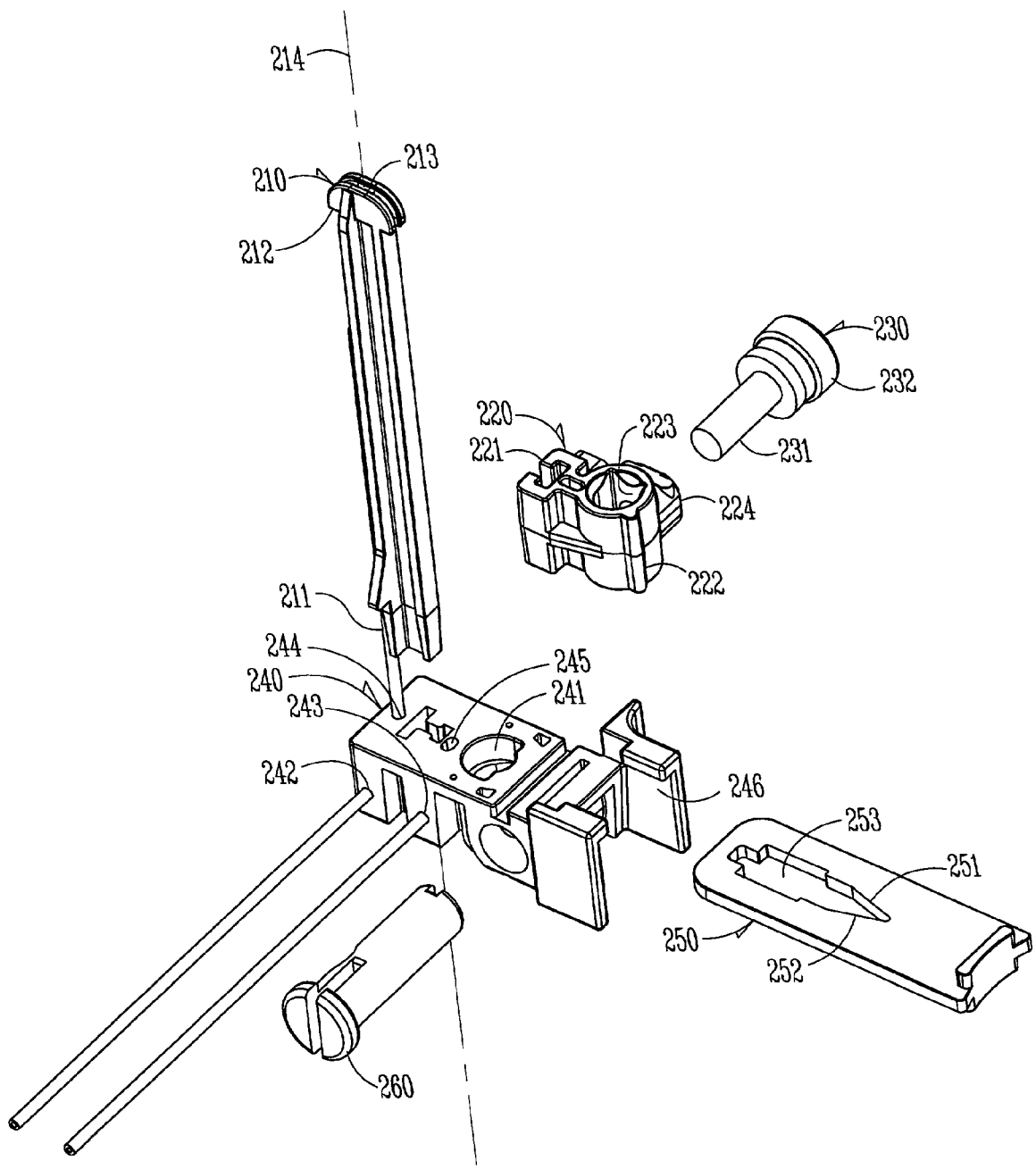
FIG. 2 shows an exploded view of the introducer device of FIG. 1.

FIGS. 1 and 2 show an introducer 100 according to the invention. A first cable housing 110 and a second cable housing 120 are also shown in FIG. 1 with a cable 130 running through both the first cable housing 110 and the second cable housing 120. When designed for MR imaging use, all materials used in this embodiment must be compatible with the MR tube environment. Specifically the materials used with MR imaging are non-magnetic. Some metals may be used, such as titanium or copper, or various polymer materials may be used.

FIG. 2 shows an exploded view of the introducer 100. The introducer includes a slide tower 210, the slide tower having an attachment end 211 and a cable guide end 212. The slide tower 210 is attached at the attachment end 211 to a body 240. The body contains a first body interface 242 that accepts the first cable housing 110 and a second body interface 243 that accepts the second cable housing 120. In this embodiment, the first cable housing is routed into the body 240 at the first body interface 242, and out of the body at a third body interface 244. The first cable housing 110 then routes along the slide tower 210 and butts up against the cable guide end 212. The second cable housing 120 routes partially into the body 240, and butts up against the body 240 at the second body interface 243.

A holder assembly 220 is attached to the slide tower 210, and allowed to along a sliding axis 214 between the body 240 and the cable guide end 212 of the slide tower 210 in a range of linear motion. The holder assembly 220 is comprised of a channel portion 221 that slidably engages the slide tower 210. The holder assembly also comprises a primary device holder portion 222 that comprises a holder hole 223 through its center. The holder hole 223 aligns with the sliding axis 214 of the slide tower 210. A set screw 230 screws into the holder assembly 220 in a threaded side hole 224. The set screw is comprised of a knob portion 232 and a threaded portion 231.

The cable 130 routes in to the introducer 100 through the first cable housing 110 passing through the body 240 at the first body interface 242 and out the third body interface 244. When the cable reaches the cable guide end 212 of the slide tower 210 it exits the first cable housing 110 and the bare cable 130 routes over the cable guide end along a groove 213 then travels back down the slide tower 210. The bare cable 130 is attached to the holder assembly 220 then continues down the slide tower 210 where it enters a fourth body interface 245. The cable 130 then enters the second cable housing 120 at the second body interface 243, and exits the introducer 100, While a push-pull cable configuration is described in this embodiment, other cable configurations are possible within the scope of the invention. For instance, a rotating cable similar to a speedometer cable could be used to actuate a mechanism such as a worm gear drive.

The body 240 further includes a guide hole 241 that passes through the body 240 parallel to the sliding axis 214. An attachment pin 260 passes through the body 240 and is used to secure the introducer 100 to a trajectory guide that will be described later. A centering plate 250 is also included with the introducer 100, and is slidably attached to the body 240 by a groove 246. The centering plate defines an opening 253. The opening 253 includes a first wall 251 and a second wall 252 that are at an angle to each other.

Figure 3:
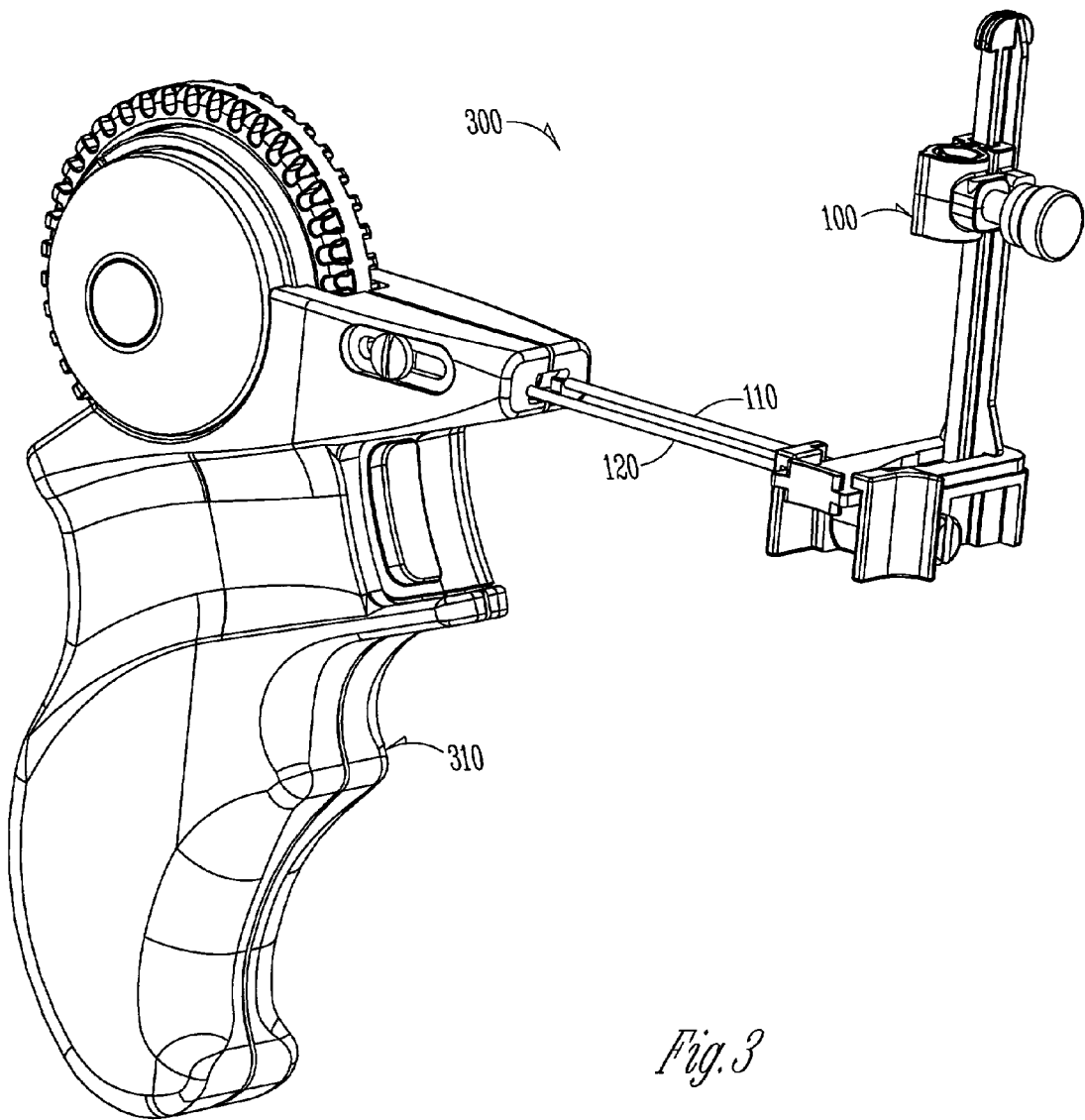
FIG. 3 shows a perspective view of a remote introducer including an advancer according to the invention.

FIG. 3 shows a complete remote introducer 300 according to the invention. The remote introducer includes an introducer 100 and a remote advancer 310. The remote advancer 310 is coupled to the introducer 100 by the first cable housing 110 and the second cable housing 120 with the cable 130 running through the introducer as described above.

Several configurations of remote advancers are possible within the scope of the invention. One embodiment could include a crank operated advancer similar to a fishing reel. Another embodiment could include both a coarse adjustment advancer and a fine adjustment advancer. Another embodiment could include a ratcheting mechanism that is advanced by a trigger. One skilled in the art will recognize that potential configurations such as these may be interchanged and still fall within the scope of the invention. In the following embodiment, the advancer includes a thumb wheel.

Figure 4:
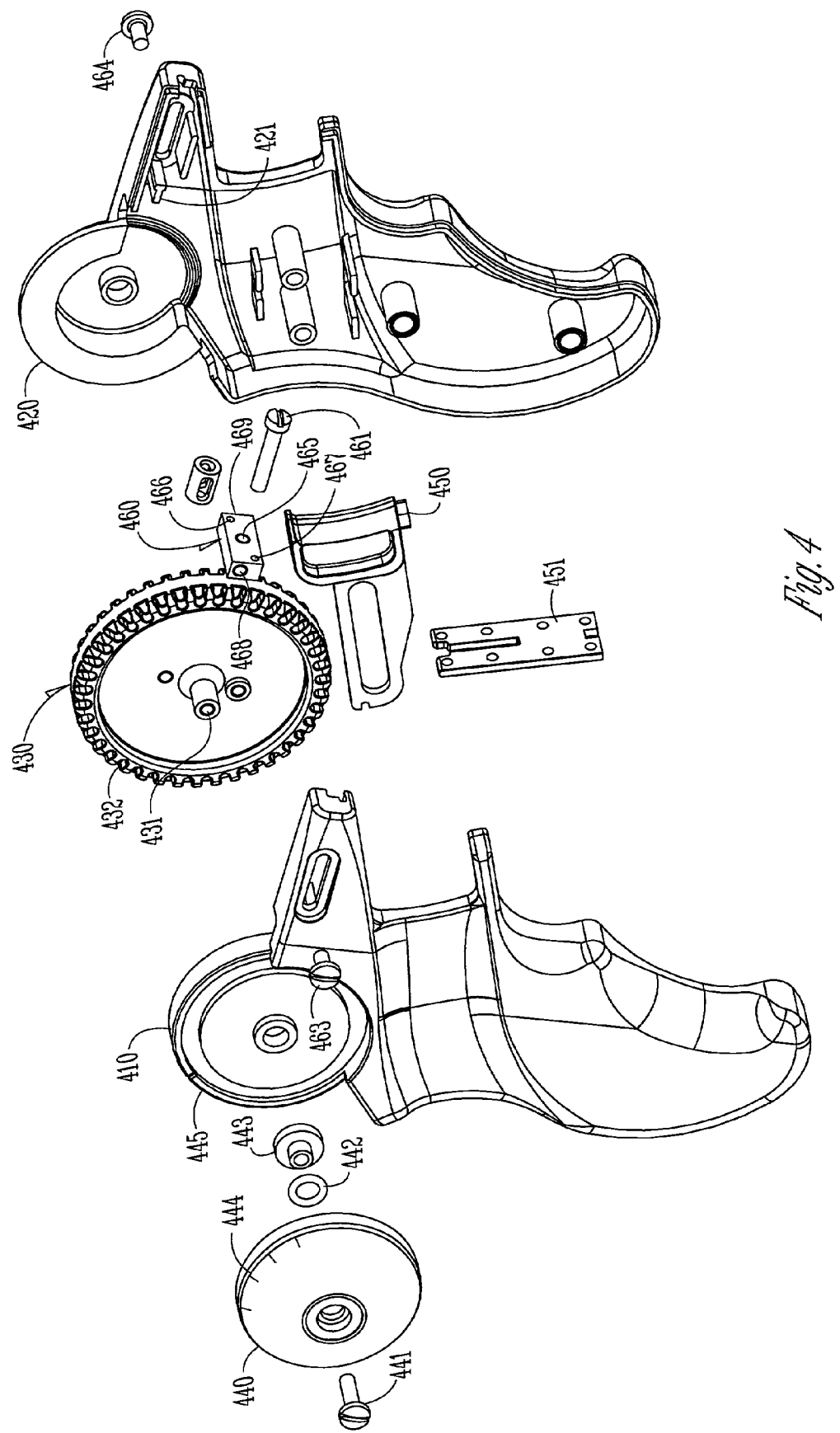
FIG. 4 shows an exploded view of the advancer from FIG. 3.

FIG. 4 shows an exploded view of the advancer 310. A first grip portion 410 and a second grip portion 420 are attached together to form a grip. A thumb wheel 430 is located between the first grip portion 410 and the second grip portion 420 and is allowed to rotate. A cable stop 460 is located next to the thumb wheel 430. The cable stop comprises a threaded adjusting hole 465, a first cable hole 466 and a second cable hole 467. The first threaded adjusting hole 465 accepts an adjusting screw 461. The cable stop further includes a first threaded hole 468 and a second threaded hole 469 for accepting a first set screw 463 and a second set screw 464.

The first cable housing 110 comes from the introducer 100 and butts against the first cable hole 466. Likewise, the second cable housing comes from the introducer 100 and butts against the second cable hole 467. The cable 130 runs through the introducer 100 as described above, and runs through the cable stop 460 at the first and second cable holes 466 and 467. The bare cable 130 is then wrapped around a thumb wheel barrel 431 located at the center of the thumb wheel 430. The portion of the cable exiting the first cable housing 110 is wrapped around the barrel 431 in one direction, while the portion of the cable exiting the second cable housing 120 is wrapped around the barrel 431 in an opposing direction. The cable 130 is fastened to the thumb wheel 430 after being wrapped around the barrel 431. The cable tension is adjusted by tightening the adjusting screw 461 against a screw stop 421.

The thumb wheel 430 also contains an array of teeth 432 on its outer edge. An engager 451 meshes with the array of teeth 432 to lock rotation of the thumb wheel 430 when not in operation. A locking trigger 450 controls the engager 451. Both the locking trigger and the engager are biased in a resting position by an elastic band (not shown) The engager is biased against the array of teeth 432 which keeps the advancer 310 in a "normally locked" state.

An indicator molding 440 is also included with the advancer 310. It is attached to the advancer 310 by and indicator screw 441 that passes through the indicator molding 440, through an o-ring 442, and through a bushing 443. The indicator molding 440 includes an array of markings 444 that may be aligned with a reference mark 445 on the first grip portion 410.

Figure 5A:
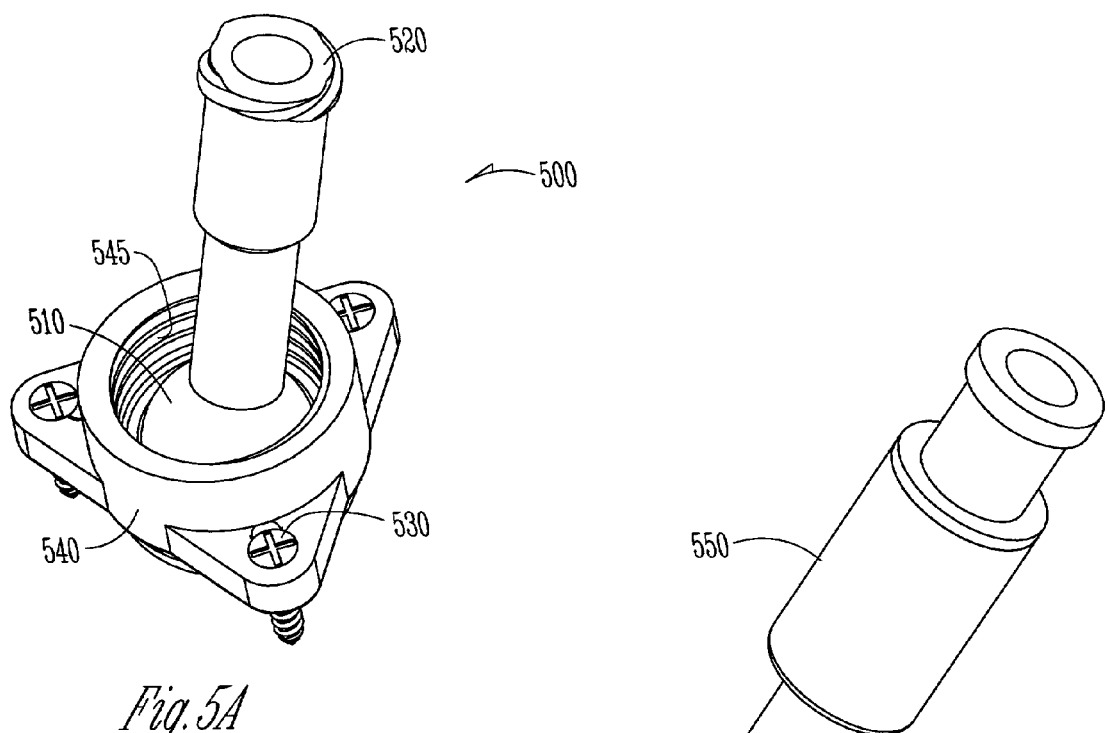
FIG. 5a shows a perspective view of a trajectory guide.
Figure 5B:
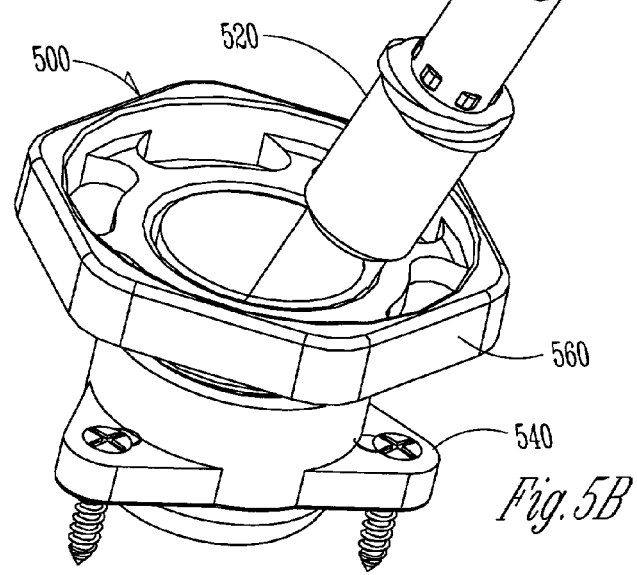
FIG. 5b shows a perspective view of a trajectory guide with an alignment tube and locking ring.
Figure 6:
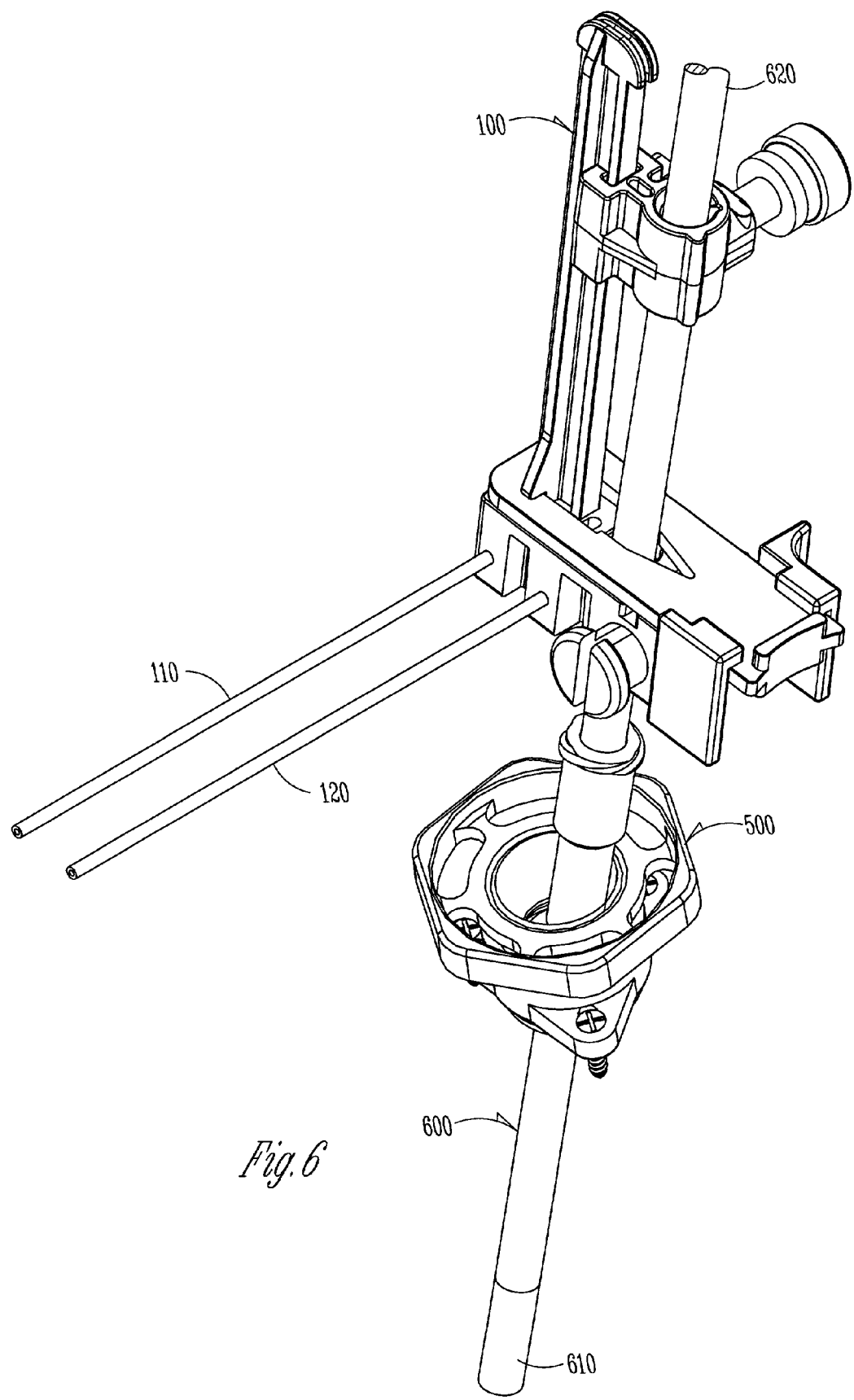
FIG. 6 shows a perspective view of an introduction system according to the invention.

The remote introducer 300 from FIG. 3 may be used as part of an introduction system as shown in FIG. 6. The introduction system includes a trajectory guide 500 as shown in FIGS. 5a and 5b. The trajectory guide 500 includes a guide base 540 with a number of screw holes at the outer edges of the guide base and a socket 545 in the center of the guide base 540. A stem 520 is attached to the guide base by a ball 510 that fits into the socket 545 to form a ball and socket joint. FIG. 5b shows an alignment tube 550 that is inserted in the stem 520 only during alignment, then it is removed. A lockring 560 is also shown that fixes the alignment of the stem in a desired position.

The introduction system shown in FIG. 6 includes a trajectory guide 500, an introducer 100 and a primary medical device 600. The introducer shown in FIG. 6 is a remote introducer 300, however, the advancer 310 is not shown. The primary medical device 600 includes a distal end 610 and a proximal end 620. The active end of the primary medical device is the distal end 610, which may be an MR microcoil, a drug delivery system, an electrode, etc.

One of ordinary skill in the art will recognize that although the invention described is designed to be compatible with an MR environment, the invention is also capable of being used without an MR imaging system. Certain aspects of the invention such as cable and mounting screw materials only need to be MR compatible if the invention is used in an MR environment. All MR compatible materials are capable of being used outside an MR environment.

In magnetic resonance imaging operation, the guide base 540 of the trajectory guide 500 is attached to the patient, for example to the patient's skull. The guide base 540 is attached using screws made from, for example, titanium metal. The alignment tube 550 is inserted into the stem 520, and the patient is placed in an MR tube. The alignment tube 550 is visible in the MR scan, along with the patient's brain. The stem 520 is aligned by using the alignment tube 550, and once it is aligned with an area of interest in the patient's brain, the stem 520 is locked in place using the locking ring 560 and the alignment tube 550 is removed.

The introducer 100 is then attached to the stem 520 and the primary medical device 600 is threaded through the holder assembly hole 223, through the centering plate 250, and into the guide hole 241 of the body 240. Once the primary medical device 600 is threaded into place, it is clamped in the holder assembly using the set screw 230. Next, the centering plate 250 is moved in its groove 246 towards the slide tower 210, and into contact with the primary medical device 600. The first wall 251 and the second wall 252 of the opening 253 contact the primary medical device 600 at two tangent points, and the walls 251 and 252 push the primary medical device 600 into the center of the guide hole 241 in the body 240. Then, a marking in the array of markings 444 on the indicator molding 440 is aligned with the reference marking 445 on the advancer 310. The indicator molding now shows a reference point of where motion of the primary medical device began.

While monitoring the patient in real time in the MR tube, the surgeon first unlocks the advancer by depressing the locking trigger 450. The primary medical device is then advanced into the patient by rotating the thumb wheel 430. The indicator molding 440 rotates with the thumb wheel 430 and shows the surgeon how far the primary medical device has moved into the patient. The position of the primary medical device can also be viewed using the MR image generated by the MR tube.

When the locking trigger 450 is fully depressed and held down, the advancer is in a "free wheeling" mode, and the thumb wheel can be moved as little or as much as is desired. If the locking trigger is depressed ½ way down, the advancer is in a "discrete step" mode. In the discrete step mode, the thumb wheel will click as each tooth of the array 432 passes the engager 451. Each discrete step is equal to ½ millimeter of travel of the primary medical device. It should be noted, however, that the distance traveled in a discrete step could be any of a number of distances.

Figure 7:
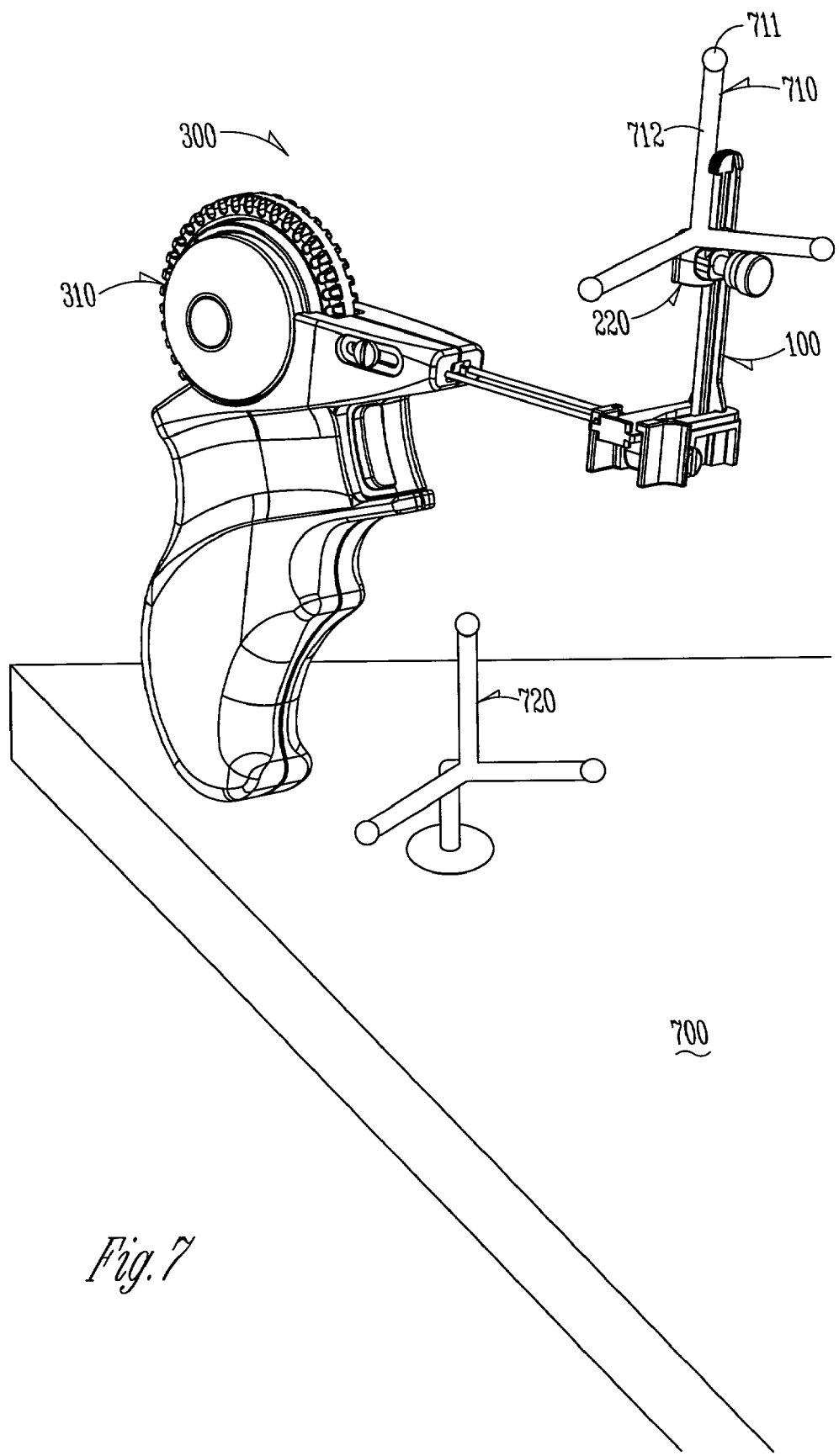
FIG. 7 shows an introduction system including a frameless reference system.

A further embodiment of the introduction system is shown in FIG. 7. The remote introducer 300 shown in the figure may include a first frameless reference attachment 710. The first frameless reference attachment is attached to the holder assembly 220 of the introducer 100. The first frameless reference attachment includes a number of balls 711 attached to a number of arms 712. Each ball 711 is reflective to infrared (IR) light. A second frameless reference attachment 720 is attached to a table 700 that the patient is attached to.

In place of the number of balls, one or more non-magnetic coils may be attached to the first and second frameless reference attachments 710 and 720. The coils are electrically influenced by the magnetic field in the MR tube and each coil defines a line in three-dimensional space. Because a coil defines a line in space as opposed to a point defined by a ball, only two coils are necessary to define a three-dimensional reference frame.

In operation, the surgeon may use the first and second frameless reference attachments 710 and 720 with an IR camera and IR light source (not shown). The patient is attached to the table 700, and the position of the table is referenced by the second frameless reference attachment 720. IR light from the IR light source is reflected off of the balls 711 and detected by the IR camera. The position of the primary medical device is known in relation to the patient by comparing the location of the first frameless reference attachment 710 to the location of the second frameless reference attachment 720.

In another embodiment, the balls 711 may include IR light generating LED devices. In this embodiment, only the IR sensitive camera is needed to detect the location of the first and second frameless reference attachments 710 and 720.

If the non-magnetic coils are used, no IR generating or sensing equipment is necessary. Only a user interface device is needed that monitors the electrical characteristics of the coils and translates the electrical characteristics into a three dimensional reference frame.

Figure 8:
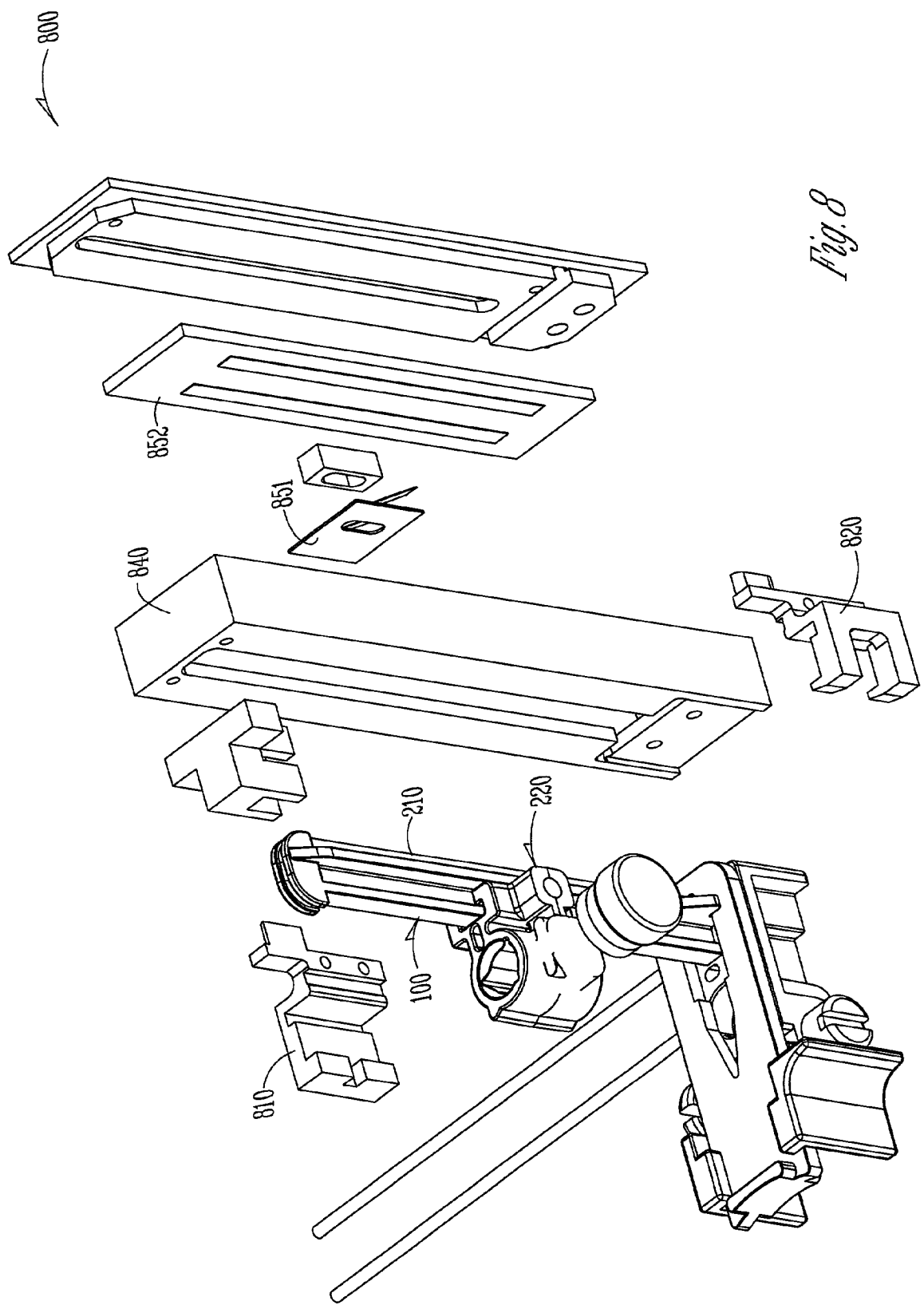
FIG. 8 shows a perspective, partially exploded view of a calibrated introducer device.

In a further embodiment, shown in FIG. 8, a local position sensor 800 is attached to the introducer 100. In the embodiment shown, the local position sensor comprises a potentiometer, however, it should be recognized that a linear encoder or similar device could be used. A first clamp 810 and a second clamp 820 are attached to the holder assembly 220. The first and second clamps 810 and 820 are then attached to a sensor slide 840 and allowed to move up and down the sensor slide 840 as the holder assembly 220 moves up and down the slide tower 210. The potentiometer consists of a first electrode 851 that is attached to the clamps 810 and 820, and a second electrode 852 that is fixed on the back of the sensor slide 840. An electrical relationship of the two electrodes 851 and 852 changes as the holder assembly moves up and down in its range of motion, and this electrical relationship is translated into an accurate position of the holder assembly. The local position sensor 800 is used as a more accurate indicator than the indicator molding 440. The accuracy of the indicator molding 440 is affected by factors such as cable stretch that the local position sensor 800 is not affected by.

Figure 9:
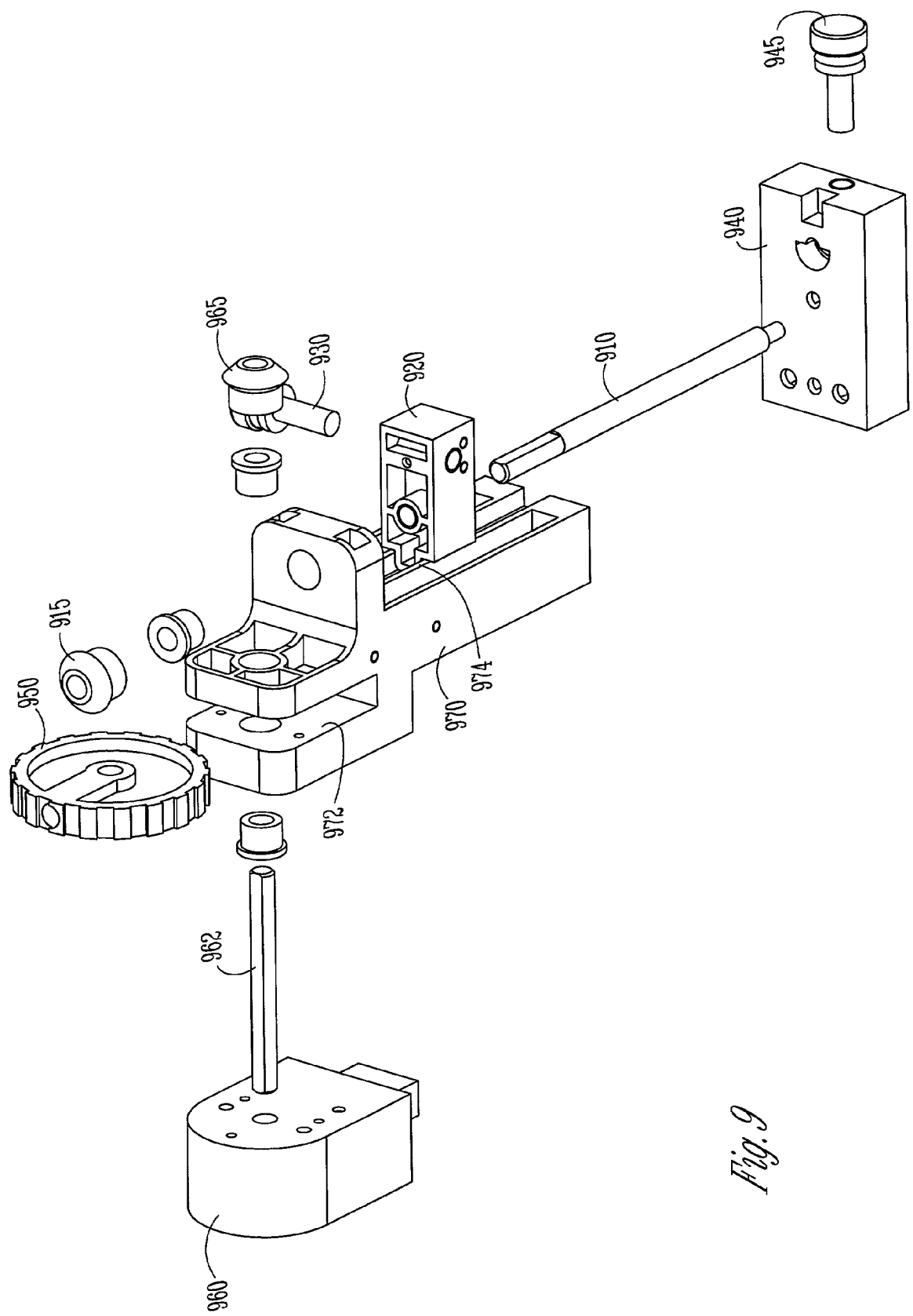
FIG. 9 shows an exploded view of a non-remote introducer device according to the invention.

In a further embodiment, shown in FIG. 9, a local introducer is shown. The local introducer is comprised of a base 940 that may be attached to a trajectory guide 500 by using a base set screw 945. A slide tower 970 is attached to the base 940. The slide tower 970 includes a holder assembly groove 974 and an advancer wheel groove 972. A holder assembly 920 slides in the holder assembly groove 974, and the position of the holder assembly is fixed by a threaded bar 910. A set screw 930 is used to clamp a primary medical device in place within the holder assembly 920. An advancer wheel 950 is located in the advancer wheel groove 972, and attached to an encoder axle 962. The encoder axle is also attached to an encoder 960 and a first drive gear 965. A second drive gear 915 connects the threaded bar 910 with the encoder axle 962.

In operation, the advancer wheel 950 is rotated a desired amount. Rotation of the advancer wheel drives the encoder 960, and the first drive gear 965. The first drive gear 965 in turn drives the second drive gear 915 which drives the threaded bar 910. The threaded bar 910 moves the holder assembly 920 along the holder assembly groove 974. The encoder is calibrated to deliver an electrical signal to a remote display (not shown) that corresponds to a holder assembly location.

Although specific embodiments have been illustrated and described herein, it will be appreciated by those skilled in the art that any arrangement which is calculated to achieve the same purpose may be substituted for the specific embodiment shown. This application is intended to cover any adaptations of variations of the present invention. It is to be understood that the above description is intended to be illustrative, and not restrictive. The scope of the invention includes any other applications in which the above structures and fabrication methods are used. The scope of the invention should be determined with reference to the appended claims, along with the full scope of equivalents to which such claims are entitled.

What is claimed is:

1. An introducer device, comprising:
   a guide unit defining a range of motion;
   a holder assembly capable of receiving attachment of a primary medical device, the holder assembly traveling along the range of motion of the guide unit; and
   a pistol grip housing comprising:
      a handheld advancer assembly operably connected to the guide unit; and
      a thumb wheel advancer system connected to the handheld advancer assembly and located remote from the guide unit, a thumb wheel operable to be rotated around a thumb wheel axis, wherein the thumb wheel advancer system translates rotation of the thumb wheel about the thumb wheel axis into motion of the holder assembly along the range of motion.

2. The introducer device of claim 1 wherein the guide unit comprises a slide tower and the range of motion is linear along a slide axis of the slide tower.

3. The introducer device of claim 1 further comprising an indicator scale coupled to the thumb wheel wherein the indicator scale indicates the position of the holder assembly within the range of motion.

4. The introducer device of claim 1 further comprising a body, the body having a hole through it, wherein the guide unit is coupled to the body and the primary medical device passes through the hole in the body as guided by the holder assembly along the range of motion.

5. The introducer device of claim 4 further comprising a centering plate adjustably attached to the body, the centering plate comprising:
   at least two walls partially defining an opening in the plate;
   wherein the centering plate may be adjusted such that the walls engage the primary medical device and center the primary medical device.

6. The introducer device of claim 1 further comprising a locking device positioned on the handheld advancer assembly and configured to allow simultaneous operation of the thumb wheel and the locking device with a hand of a user, wherein the locking device must be actuated before any motion of the holder assembly is permitted.

7. The introducer device of claim 6 wherein the locking device may further be selectively actuated in either a freewheeling mode or a discrete step mode.

8. The introducer device of claim 6, wherein the handheld advancer assembly has a handheld pistol grip configuration;
   wherein the thumb wheel axis is defined relative to the handheld advancer assembly to allow operation of the thumb wheel with a thumb of a user and the locking device is operable to be operated with a digit of a user simultaneously.

9. The introducer device of claim 1, further comprising a first frameless locating attachment coupled to the holder assembly.

10. The introducer device of claim 9, wherein the first frameless locating attachment includes a plurality of infrared (IR) reflective spheres.

11. The introducer device of claim 9, wherein the first frameless locating attachment includes a plurality of infrared (IR) generating LED devices.

12. The introducer device of claim 1, further comprising:
   an MR compatible cable that operably couples the handheld advancer assembly to the holder assembly, wherein input from the handheld advancer assembly controls motion of the holder assembly along the range of motion.

13. The introducer device of claim 1, further comprising:
   a cable having a first end attached to a first side of the thumb wheel and a second end attached to a second side of the thumb wheel, wherein the thumb wheel is rotated to move the cable in at least one of two directions.

14. The introduction system of claim 13, wherein the introducer device has a handheld pistol grip configuration;
   wherein an adjusting wheel axis is defined relative to the introducer device to allow operation of the adjusting wheel with a thumb of a user and a locking device is operable to be operated with a digit of a user simultaneously.

15. The introducer device of claim 1, wherein the pistol grip housing further includes:
   a pistol grip configured housing operable to be supported and held in a hand of a user including a first portion formed at an angle relative to a second portion; and a trigger member mounted in the pistol grip configured housing;

wherein the thumb wheel advancer and the trigger member are both mounted and positioned in the pistol grip configured housing to allow simultaneous operation of both the thumb wheel advancer and the trigger member simultaneously.

16. An introduction system, comprising:
a trajectory guide device;
a primary medical device;
an introducer device associated with the trajectory guide and supported by a user, comprising:
  a guide unit having a range of motion along a first axis;
  a holder assembly capable of receiving attachment of the primary medical device, the holder assembly traveling along the range of motion of the guide unit;
  a rotating wheel advancer located remote from the guide unit; and
  an MR compatible cable that operably couples the rotating wheel advancer to the holder assembly, wherein input from the rotating wheel advancer controls motion of the holder assembly along the range of motion by moving the cable along a second axis different from the first axis.

17. The introduction system of claim 16, wherein the introducer device further comprises:
  a local position sensor mounted to the guide unit, wherein a position of the holder assembly along the range of motion is sensed; and
  a remote user interface, operably coupled to the local position sensor, wherein the remote user interface displays the position of the holder assembly along the range of motion.

18. The introduction system of claim 16, further comprising:
  at least one device mounted coil that determines a holder assembly reference frame; and
  a user interface that detects the holder assembly reference frame and an operating surface reference frame and determines a relative position difference between the two reference frames.

19. The introduction system of claim 16, further comprising:
  a first frameless locating attachment attached to the holder assembly;
  a second frameless locating attachment attached to a surface that a patient is attached to; and
  an imaging device that detects the first and second frameless locating attachments and references the position of the first frameless locating attachment relative to the second frameless locating attachment.

20. The introduction system of claim 19, wherein the first and second frameless locating attachments includes at least one of a plurality of infrared (IR) reflective spheres; a plurality of infrared (IR) generating LED devices; or combinations thereof.

21. The introduction system of claim 19, wherein the imaging device includes an IR sensitive camera.

22. The introduction system of claim 16, wherein the introducer device has a handheld pistol grip configuration;
wherein a rotating wheel advancer axis is defined relative to the introducer device to allow operation of the rotating wheel with a thumb of a user and a locking device is operable to be operated with a digit of a user simultaneously.

23. The introduction system of claim 16, further comprising:
  a fixation member operable to fix the trajectory guide directly to a patient.

24. An introduction system comprising:
a trajectory guide device and a fixation member, wherein the trajectory guide device is attached directly to a patient with the fixation member;
an introducer device attached to the trajectory guide, comprising:
  a guide unit having a range of motion;
  a holder assembly capable of receiving attachment of a primary medical device, the holder assembly traveling along the range of motion of the guide unit; and
  a user supported housing attached to an adjusting wheel system including a thumb wheel coupled locally to the guide unit, wherein the thumb wheel is operable to rotate around an axis of rotation and the adjusting wheel system translates the rotary motion of the thumb wheel around the axis of rotation into substantially linear motion of the holder assembly along the range of motion; and
a primary medical device attached to the holder assembly.

25. The introduction system of claim 24, wherein the introducer device further comprises:
  a local position sensor mounted to the guide unit, wherein a position of the holder assembly along the range of motion is sensed; and
  a remote user interface, operably coupled to the local position sensor, wherein the remote user interface displays the position of the holder assembly along the range of motion.

26. The introduction system of claim 25, wherein the local position sensor includes at least one of a potentiometer, an encoder, or combinations thereof.

27. A method of introducing a primary medical device into a patient with at least a guide unit, a holder assembly, and an advancer, comprising:
  attaching the guide unit to the patient;
  attaching the primary medical device to the holder assembly;
  coupling a cable to the holder assembly;
  coupling the cable to a wheel advancer of the advancer;
  supporting the wheel advancer by a user;
  positioning the wheel advancer at a location remote from the guide unit;
  rotating the wheel advancer around a fixed axis to form tension on at least one of the cable or the holder assembly, wherein the tension applies a force to the holder thus moving the holder assembly along a range of motion defined by the guide unit;
  wherein the cable translates non-coaxially with the holder assembly.

28. The method of claim 27, wherein attaching the guide unit to the patient, further comprises:
  attaching a trajectory guide to the patient;
  aligning the trajectory guide; and
  attaching the guide unit to the trajectory guide.

29. The method of claim 27, further comprising:
  acquiring an image of a portion of the patient with the cable within the portion of the patient being imaged;
  wherein the image of the portion of the patient is unaffected by the cable.

30. A calibrated introducer device, comprising:
an advancer assembly sized and configured to be supported in a single hand of a user, including:
  a guide unit defining a range of motion;
  a holder assembly capable of receiving attachment of a primary medical device, the holder assembly traveling along the range of motion of the guide unit; and
  a thumb wheel advancer including a thumb wheel located remote from the guide unit and operable to be moved with a thumb of the single hand;
an MR compatible cable that operatively couples the thumb wheel to the holder assembly, wherein input from the thumb wheel controls motion of the holder assembly along the range of motion;
a local position sensor mounted to the guide unit, wherein a position of the holder assembly along the range of motion is sensed; and
a remote user interface, operably coupled to the local position sensor, wherein the remote user interface displays the position of the holder assembly along the range of motion.

31. The calibrated introducer device of claim 30, wherein the MR compatible cable is a push-pull cable.

32. The calibrated introducer device of claim 30, wherein the local position sensor includes a potentiometer.

33. The calibrated introducer device of claim 30, wherein the local position sensor includes an encoder.

34. The calibrated introducer device of claim 30, wherein the advancer assembly further includes:
  a pistol grip configured housing operable to be held in a hand of a user including a first portion formed at an angle relative to a second portion; and
  a trigger member mounted in the pistol grip configured housing;
  wherein the MR compatible cable passes through the first portion to engage the thumbwheel;
  wherein the thumb wheel advancer and the trigger member are both mounted and positioned in the pistol grip configured housing to allow simultaneous operation of both the thumb wheel advancer and the trigger member simultaneously.

35. An introducer device, comprising:
a guide assembly including:
  a guide unit defining a range of motion;
  a holder assembly adapted to be connected to a primary medical device, wherein the holder assembly is adapted to move along the guide unit over at least a portion of the range of motion;
  a body defining a through hole, wherein the guide unit is coupled to the body and the primary medical device is operable to pass through the through hole in the body; and
a primary medical device positioning plate adjustably attached to the body and operable to engage the primary medical device to substantially position the primary medical device within the through hole; and
a handheld advancer assembly supported by a user including:
  a pistol grip portion operable to be held within a hand of the user;
  a thumb wheel advancer system connected to the pistol grip portion and located remote from the guide unit including a thumb wheel operable to be moved with a thumb of the user;
  a trigger member connected to the pistol grip portion operable to be actuated by a digit of the user to engage the thumb wheel to allow restricted movement of the thumb wheel or disengage the thumb wheel to allow free wheel movement of the thumb wheel; and
  a cable having a first end that extends from a first side of the thumb wheel and a second end that extends from a second side of the thumb wheel and a middle portion that couples to the holder assembly, wherein movement of the thumb wheel controls motion of the holder assembly along the range of motion;
wherein the thumb wheel rotates around a thumb wheel axis;
wherein the thumb wheel advancer system translates rotation of the thumb wheel about the thumb wheel axis into motion of the holder assembly along the range of motion.

* * * * *

UNITED STATES PATENT AND TRADEMARK OFFICE
CERTIFICATE OF CORRECTION

PATENT NO.        : 7,660,621 B2
APPLICATION NO.   : 09/827266
DATED             : February 9, 2010
INVENTOR(S)       : Skakoon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1754 days.

Signed and Sealed this

Thirtieth Day of November, 2010

David J. Kappos
*Director of the United States Patent and Trademark Office*